(12) United States Patent
Vahala et al.

(10) Patent No.: US 11,160,608 B2
(45) Date of Patent: Nov. 2, 2021

(54) MEDICAL INSTRUMENT WITH MULTIPLE DISPLAYS FOR CONTROLLING A TREATMENT SYSTEM

(71) Applicant: KONINKLIJKE PHILIPS N.V., Eindhoven (NL)

(72) Inventors: Erkki Tapani Vahala, Eindhoven (NL); Jari Matti Ilmari Salminen, Eindhoven (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 192 days.

(21) Appl. No.: 14/912,427

(22) PCT Filed: Aug. 22, 2014

(86) PCT No.: PCT/EP2014/067919
§ 371 (c)(1),
(2) Date: Feb. 17, 2016

(87) PCT Pub. No.: WO2015/025039
PCT Pub. Date: Feb. 26, 2015

(65) Prior Publication Data
US 2016/0192991 A1    Jul. 7, 2016

(30) Foreign Application Priority Data
Aug. 23, 2013   (EP) .................................... 13181448

(51) Int. Cl.
*A61B 34/10*          (2016.01)
*A61B 34/30*          (2016.01)
(Continued)

(52) U.S. Cl.
CPC .............. *A61B 34/10* (2016.02); *A61B 6/03* (2013.01); *A61B 8/00* (2013.01); *A61B 34/25* (2016.02);
(Continued)

(58) Field of Classification Search
CPC ........ A61B 2034/107; A61B 2034/254; A61B 2090/372; A61B 2090/374; A61B 34/10;
(Continued)

(56) References Cited

U.S. PATENT DOCUMENTS 6,618,620 B1 * 9/2003 Freundlich ............... A61N 7/02
600/437
7,809,838 B2   10/2010 Da Palma
(Continued)

FOREIGN PATENT DOCUMENTS

EP       2042126 A1   1/2009
JP   2009089398 A     4/2009
(Continued)

OTHER PUBLICATIONS

Resource Locking, Webopedia Computer Dictionary, Jun. 2012.*

*Primary Examiner* — Yi-Shan Yang
(74) *Attorney, Agent, or Firm* — Sherry Austin

(57) ABSTRACT

The invention provides for a medical instrument (700, 800) comprising: a first display device (200), a second display device (754), a database (768), and a processor (746). Execution of instructions cause the processor to: receive (900) a medical image (102, 102', 102", 102'"); display (902) the medical image in a physician graphical user (202, 1000) interface using the first display device and on a technician graphical user interface (100, 1000) using the second display device. Execution of the instructions causes the processor to repeatedly: receive (906) planning data (764) from the physician graphical user interface, display (908) the planning data on the technician graphical user interface; receive (910) treatment plan data (766) from the technician graphical user interface; store (912) the treatment plan data in the database; and generate (914) control data
(Continued)

(770, 772) for controlling a treatment system using the treatment plan data in the database.

20 Claims, 9 Drawing Sheets

(51) Int. Cl.
    *G16H 40/63*     (2018.01)
    *A61N 7/02*     (2006.01)
    *A61B 34/00*     (2016.01)
    *A61B 6/03*     (2006.01)
    *A61B 8/00*     (2006.01)
    *A61N 7/00*     (2006.01)
    *G06F 3/0484*     (2013.01)
    *G06T 7/00*     (2017.01)
    *A61B 90/00*     (2016.01)

(52) U.S. Cl.
    CPC ............... *A61B 34/30* (2016.02); *A61N 7/00* (2013.01); *A61N 7/02* (2013.01); *G06F 3/04842* (2013.01); *G06T 7/0012* (2013.01); *G16H 40/63* (2018.01); *A61B 2034/107* (2016.02); *A61B 2034/254* (2016.02); *A61B 2090/372* (2016.02); *A61B 2090/374* (2016.02); *A61N 2007/0078* (2013.01); *A61N 2007/0095* (2013.01); *A61N 2007/025* (2013.01); *G06T 2207/10088* (2013.01); *G06T 2207/10132* (2013.01)

(58) Field of Classification Search
    CPC ........... A61B 34/25; A61B 34/30; A61B 6/03; A61B 8/00; A61N 2007/0078; A61N 2007/0095
    See application file for complete search history.

(56) References Cited

U.S. PATENT DOCUMENTS

| | | |
|---|---|---|
| 2004/0181115 A1 | 9/2004 | Sandyk |
| 2008/0154253 A1* | 6/2008 | Damasco ............... A61B 18/02 606/20 |
| 2009/0089081 A1* | 4/2009 | Haddad ................ A61B 17/157 705/2 |
| 2011/0208055 A1* | 8/2011 | Dalal ...................... A61N 7/02 600/439 |
| 2012/0066643 A1 | 3/2012 | McRae |
| 2013/0055147 A1 | 2/2013 | Vasudev |
| 2013/0096575 A1* | 4/2013 | Olson ................... G06T 19/003 606/130 |
| 2013/0172906 A1* | 7/2013 | Olson ................... A61B 34/71 606/130 |
| 2013/0262423 A1* | 10/2013 | Graefe ............. G06F 17/30362 707/703 |

FOREIGN PATENT DOCUMENTS

| | | |
|---|---|---|
| WO | 2011123669 A1 | 10/2011 |
| WO | 2013030746 A1 | 3/2013 |

* cited by examiner

MEDICAL INSTRUMENT WITH MULTIPLE DISPLAYS FOR CONTROLLING A TREATMENT SYSTEM

CROSS REFERENCE TO RELATED APPLICATIONS

This application is a U.S. national phase application of International Application No. PCT/EP2014/067919, filed on Aug. 22, 2014, which claims the benefit of EP Application Serial No. 13181448.5 filed on Aug. 23, 2013 and is incorporated herein by reference.

TECHNICAL FIELD

The invention relates to the control of treatment systems, in particular the use of multiple graphical user interfaces to control a high intensity focused ultrasound system.

BACKGROUND OF THE INVENTION

Ultrasound from a focused ultrasonic transducer can be used to selectively treat regions within the interior of the body. Ultrasonic waves are transmitted as high energy mechanical vibrations. These vibrations induce tissue heating as they are damped, and they can also lead to cavitation. Both tissue heating and cavitation can be used to destroy tissue in a clinical setting. However, heating tissue with ultrasound is easier to control than cavitation. Ultrasonic treatments can be used to ablate tissue and to kill regions of cancer cells selectively. This technique has been applied to the treatment of uterine fibroids, and has reduced the need for hysterectomy procedures.

To selectively treat tissue, a focused ultrasonic transducer can be used to focus the ultrasound on a particular treatment or target volume. The transducer is typically mounted within a medium, such as degassed water, that is able to transmit ultrasound. Actuators are then used to adjust the position of the ultrasonic transducer and thereby adjust the tissue region that is being treated. The guiding of ultrasound therapy using magnetic resonance imaging is known.

During ultrasound therapy, ultrasound is typically focused into different sonication volumes or cells. The duration of the sonication can be as long as several minutes. Typically a technician will monitor the progress of the sonication. During the sonication of a sonication cell, a decision as to which sonication cell to sonicate next is often made manually by the technician. A physician looking over the shoulder of the technician may provide verbal instructions during the course of the therapy.

United States Patent application publication US 2013/0055147 discloses a graphical user interface with a primary graphical user interface and a secondary graphical user interface. The content of the primary graphical user interface element is contextually related to the content of the secondary graphical user interface. The European patent application EP 2 042 126 shows an arrangement for generating a surgical plan. The surgical plan is remotely generated by a supplier's party's technician who (implicitly) makes use of a technician's display. The surgical plan is transferred to a healthcare facility where it is available for review by the surgeon and have the supplier party change the surgical plan. The known arrangement is intended to be used on the basis of separate versions that are accessed separately by the surgeon and the technician.

SUMMARY OF THE INVENTION

The invention provides for a medical instrument, computer program product and a method in the independent claims. Embodiments are given in the dependent claims As will be appreciated by one skilled in the art, aspects of the present invention may be embodied as an apparatus, method or computer program product. Accordingly, aspects of the present invention may take the form of an entirely hardware embodiment, an entirely software embodiment (including firmware, resident software, micro-code, etc.) or an embodiment combining software and hardware aspects that may all generally be referred to herein as a "circuit," "module" or "system." Furthermore, aspects of the present invention may take the form of a computer program product embodied in one or more computer readable medium(s) having computer executable code embodied thereon.

Any combination of one or more computer readable medium(s) may be utilized. The computer readable medium may be a computer readable signal medium or a computer readable storage medium. A 'computer-readable storage medium' as used herein encompasses any tangible storage medium which may store instructions which are executable by a processor of a computing device. The computer-readable storage medium may be referred to as a computer-readable non-transitory storage medium. The computer-readable storage medium may also be referred to as a tangible computer readable medium. In some embodiments, a computer-readable storage medium may also be able to store data which is able to be accessed by the processor of the computing device. Examples of computer-readable storage media include, but are not limited to: a floppy disk, a magnetic hard disk drive, a solid state hard disk, flash memory, a USB thumb drive, Random Access Memory (RAM), Read Only Memory (ROM), an optical disk, a magneto-optical disk, and the register file of the processor. Examples of optical disks include Compact Disks (CD) and Digital Versatile Disks (DVD), for example CD-ROM, CD-RW, CD-R, DVD-ROM, DVD-RW, or DVD-R disks. The term computer readable-storage medium also refers to various types of recording media capable of being accessed by the computer device via a network or communication link. For example a data may be retrieved over a modem, over the internet, or over a local area network. Computer executable code embodied on a computer readable medium may be transmitted using any appropriate medium, including but not limited to wireless, wireline, optical fiber cable, RF, etc., or any suitable combination of the foregoing.

A computer readable signal medium may include a propagated data signal with computer executable code embodied therein, for example, in baseband or as part of a carrier wave. Such a propagated signal may take any of a variety of forms, including, but not limited to, electro-magnetic, optical, or any suitable combination thereof. A computer readable signal medium may be any computer readable medium that is not a computer readable storage medium and that can communicate, propagate, or transport a program for use by or in connection with an instruction execution system, apparatus, or device.

'Computer memory' or 'memory' is an example of a computer-readable storage medium. Computer memory is any memory which is directly accessible to a processor. 'Computer storage' or 'storage' is a further example of a computer-readable storage medium. Computer storage is any non-volatile computer-readable storage medium. In some embodiments computer storage may also be computer memory or vice versa.

A 'processor' as used herein encompasses an electronic component which is able to execute a program or machine executable instruction or computer executable code. References to the computing device comprising "a processor" should be interpreted as possibly containing more than one processor or processing core. The processor may for instance be a multi-core processor. A processor may also refer to a collection of processors within a single computer system or distributed amongst multiple computer systems. The term computing device should also be interpreted to possibly refer to a collection or network of computing devices each comprising a processor or processors. The computer executable code may be executed by multiple processors that may be within the same computing device or which may even be distributed across multiple computing devices.

Computer executable code may comprise machine executable instructions or a program which causes a processor to perform an aspect of the present invention. Computer executable code for carrying out operations for aspects of the present invention may be written in any combination of one or more programming languages, including an object oriented programming language such as Java, Smalltalk, C++ or the like and conventional procedural programming languages, such as the "C" programming language or similar programming languages and compiled into machine executable instructions. In some instances the computer executable code may be in the form of a high level language or in a pre-compiled form and be used in conjunction with an interpreter which generates the machine executable instructions on the fly.

The computer executable code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider).

Aspects of the present invention are described with reference to flowchart illustrations and/or block diagrams of methods, apparatus (systems) and computer program products according to embodiments of the invention. It will be understood that each block or a portion of the blocks of the flowchart, illustrations, and/or block diagrams, can be implemented by computer program instructions in form of computer executable code when applicable. It is further under stood that, when not mutually exclusive, combinations of blocks in different flowcharts, illustrations, and/or block diagrams may be combined. These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks.

These computer program instructions may also be stored in a computer readable medium that can direct a computer, other programmable data processing apparatus, or other devices to function in a particular manner, such that the instructions stored in the computer readable medium produce an article of manufacture including instructions which implement the function/act specified in the flowchart and/or block diagram block or blocks.

The computer program instructions may also be loaded onto a computer, other programmable data processing apparatus, or other devices to cause a series of operational steps to be performed on the computer, other programmable apparatus or other devices to produce a computer implemented process such that the instructions which execute on the computer or other programmable apparatus provide processes for implementing the functions/acts specified in the flowchart and/or block diagram block or blocks.

A 'user interface' as used herein is an interface which allows a user or operator to interact with a computer or computer system. A 'user interface' may also be referred to as a 'human interface device.' A user interface may provide information or data to the operator and/or receive information or data from the operator. A user interface may enable input from an operator to be received by the computer and may provide output to the user from the computer. In other words, the user interface may allow an operator to control or manipulate a computer and the interface may allow the computer indicate the effects of the operator's control or manipulation. The display of data or information on a display or a graphical user interface is an example of providing information to an operator. The receiving of data through a keyboard, mouse, trackball, touchpad, pointing stick, graphics tablet, joystick, gamepad, webcam, headset, gear sticks, steering wheel, pedals, wired glove, dance pad, remote control, and accelerometer are all examples of user interface components which enable the receiving of information or data from an operator.

A 'hardware interface' as used herein encompasses an interface which enables the processor of a computer system to interact with and/or control an external computing device and/or apparatus. A hardware interface may allow a processor to send control signals or instructions to an external computing device and/or apparatus. A hardware interface may also enable a processor to exchange data with an external computing device and/or apparatus. Examples of a hardware interface include, but are not limited to: a universal serial bus, IEEE 1394 port, parallel port, IEEE 1284 port, serial port, RS-232 port, IEEE-488 port, Bluetooth connection, Wireless local area network connection, TCP/IP connection, Ethernet connection, control voltage interface, MIDI interface, analog input interface, and digital input interface.

A 'display' or 'display device' as used herein encompasses an output device or a user interface adapted for displaying images or data. A display may output visual, audio, and or tactile data. Examples of a display include, but are not limited to: a computer monitor, a television screen, a touch screen, tactile electronic display, Braille screen, Cathode ray tube (CRT), Storage tube, Bistable display, Electronic paper, Vector display, Flat panel display, Vacuum fluorescent display (VF), Light-emitting diode (LED) displays, Electroluminescent display (ELD), Plasma display panels (PDP), Liquid crystal display (LCD), Organic light-emitting diode displays (OLED), a projector, and Head-mounted display.

A Medical image may be understood as two or three dimensional data that has been acquired using a medical imaging scanner. A medical imaging scanner may be understood as a apparatus adapted for acquiring information about the physical structure of a patient and construct sets of two dimensional or three dimensional medical image data. Medical image data can be used to construct visualizations which are useful for diagnosis by a physician. This visualization can be performed using a computer.

Magnetic Resonance (MR) data may be understood as being the recorded measurements of radio frequency signals emitted by atomic spins by the antenna of a Magnetic resonance apparatus during a magnetic resonance imaging scan. Magnetic resonance data is an example of medical image data. A Magnetic Resonance Imaging (MRI) image may be understood as being the reconstructed two or three dimensional visualization of anatomic data contained within the magnetic resonance imaging data. This visualization can be performed using a computer.

MR thermometry data may be understood as being the recorded measurements of radio frequency signals emitted by atomic spins by the antenna of a Magnetic resonance apparatus during a magnetic resonance imaging scan which contains information which may be used for magnetic resonance thermometry. Magnetic resonance thermometry functions by measuring changes in temperature sensitive parameters. Examples of parameters that may be measured during magnetic resonance thermometry are: the proton resonance frequency shift, the diffusion coefficient, or changes in the T1 and/or T2 relaxation time may be used to measure the temperature using magnetic resonance. The proton resonance frequency shift is temperature dependent, because the magnetic field that individual protons, hydrogen atoms, experience depends upon the surrounding molecular structure. An increase in temperature decreases molecular screening due to the temperature affecting the hydrogen bonds. This leads to a temperature dependence of the proton resonant frequency.

The proton density depends linearly on the equilibrium magnetization. It is therefore possible to determine temperature changes using proton density weighted images.

The relaxation times T1, T2, and T2-star (sometimes written as T2*) are also temperature dependent. The reconstruction of T1, T2, and T2-star weighted images can therefore be used to construct thermal or temperature maps.

The temperature also affects the Brownian motion of molecules in an aqueous solution. Therefore pulse sequences which are able to measure diffusion coefficients such as a pulsed diffusion gradient spin echo may be used to measure temperature.

One of the most useful methods of measuring temperature using magnetic resonance is by measuring the proton resonance frequency (PRF) shift of water protons. The resonant frequency of the protons is temperature dependent. As the temperature changes in a voxel the frequency shift will cause the measured phase of the water protons to change. The temperature change between two phase images can therefore be determined. This method of determining temperature has the advantage that it is relatively fast in comparison to the other methods. The PRF method is discussed in greater detail than other methods herein. However, the methods and techniques discussed herein are also applicable to the other methods of performing thermometry with magnetic resonance imaging.

An 'ultrasound window' as used herein encompasses a window which is able to transmit ultrasonic waves or energy. Typically a thin film or membrane is used as an ultrasound window. The ultrasound window may for example be made of a thin membrane of BoPET (Biaxially-oriented polyethylene terephthalate).

In one aspect the invention provides for a medical instrument comprising a first display device and a second display device. A display device as used herein encompasses an apparatus or device for displaying graphical information. The display device may also incorporate a user interface such as a graphical user interface for receiving data from the user of the display device. The display device may be a device for instance connected to a computer. In one instance a display device may be a monitor and an input device such as a mouse. In other instances the display device may be a separate computing or mobile computing device such a tablet computer. The display on a tablet computer for instance is typically touch sensitive and may be used for inputting data. The medical instrument further comprises a database.

A database as used herein encompasses a file or program for storing and retrieving data. The medical instrument further comprises a memory for storing machine-executable instructions. In some instances the database may be stored in the memory or storage device or the database may also be implemented on a separate computing device. The medical instrument further comprises a processor for executing the machine-executable instructions. Execution of the instructions causes the processor to receive a medical image. A medical image as used herein is an image which is descriptive of the internal anatomy of a subject. Execution of the instructions further cause the processor to display the medical image in a physician graphical user interface using the first display device. The term 'physician graphical user interface' is simply a label to identify a particular graphical user interface. Execution of the instructions causes the processor to display the medical image on a technical graphical user interface using the second display device. The term 'technician graphical user interface' is a label to refer to a particular graphical user interface. For instance the physician graphical user interface could also be referred to as a first graphical user interface and the technician graphical user interface could also be referred to as a second graphical user interface.

Execution of the instructions further causes the processor to repeatedly receive planning data from the physician graphical user interface. The planning data is descriptive of a location in the medical image. Execution of the instructions further cause the processor to repeatedly display the planning data on the technician graphical user interface. Execution of the instructions further causes the processor to repeatedly receive treatment plan data from the technician graphical user interface. Execution of the instructions further causes the processor to store the treatment plan data in the database. Execution of the instructions further cause the processor to generate control data for controlling the treatment system using the treatment plan data in the database. The control data as used herein encompasses commands for specifically controlling the treatment system. This embodiment may be beneficial because it facilitates the entry of data for planning and generating the control data by two separate individuals. Typically when a technician is creating a plan to control a treatment system a physician may provide guidance.

In existing systems the physician would typically look over the shoulder of the technician and explain verbally to the technician what to do. The use of two separate graphical user interfaces enables the data to be entered by the technician with less thought thereby reducing the cognitive burden. The intentions of the physician are displayed directly on the technician graphical user interface after they have been entered into the physician graphical user interface. This also reduces the chances of errors in the control data. Such an arrangement may be used for controlling a treatment system in real time. For instance, when performing high-intensity focused ultrasound various regions of the subject are sonicated sequentially. A sonication may have a duration of several minutes and during this time the technician and the physician decide on the next place to sonicate.

In some embodiments medical images are received more than once and are also repeatedly displayed on both the physician graphical user interface and the technician graphical user interface. However, this is not necessary and in some cases only a single medical image may be used.

In another embodiment execution of the instructions further cause the processor to divide at least a portion of the medical image into treatment cells. The database stores the control data for each of the treatment cells. In other words control data for controlling the treatment system is divided within the database with references to a particular treatment cell. Data for controlling the treatment system is thereby divided up with respect to particular treatment cells. Execution of the instructions further cause the processor to receive a selection of a first treatment cell using the treatment plan data. This may be referred to as a first selection. Execution of the instructions further cause the processor to lock the control data of the first treatment cell in the database to restrict modification of the control data of the first treatment cell to only the treatment plan data. This is equivalent to saying that only the technician graphical user interface may be used to modify the treatment plan data for the first treatment cell when it is locked. The reference to locking the control data in the database is equivalent to stating that transaction control is used to restrict modification of the control data. For instance the database in some embodiments may be a relational database. In such case standard tools for locking or restricting accesses to certain entries in the database may be used. For instance a transaction control language which is a subset of the SQL language may for instance be used. The data or control data for particular treatment cells may be stored in separate records within the database. If the database is a relational database then standard transitional processing control may be used to control if the control data associated with a particular treatment cell may be modified or not.

Execution of the instructions further cause the processor to modify the control data of the first treatment cell using the treatment plan data. Execution of the instructions further cause the processor to unlock the cell control data of the first treatment cell in the database after modification with the cell control data.

This embodiment may be beneficial because both the physician graphical user interface and the technician graphical user interface may be used to modify the treatment plan data in the database. However, if the technician graphical user interface is being used to modify the treatment plan data for a particular sonication cell the locking and unlocking of the cell control data for the first treatment cell will prevent it from being modified by the physician graphical user interface at the same time.

In another embodiment execution of the instructions further cause the processor to receive a selection of a second treatment cell using the planning data. This selection may be referred to as a second selection. Execution of the instructions further cause the processor to repeatedly lock the cell control data of the second treatment cell in the database during modification of the cell control data of the second treatment cell by the planning data. Execution of the instructions further cause the processor to repeatedly modify the cell control data of the second treatment cell using the planning data. Execution of the instructions further causes the processor to unlock the cell control of the second chosen treatment cell data in the database after modification with the cell control data. As with the previous embodiment this embodiment may also be implemented in a relational database and use typical control transaction processing such as a transaction control language.

In another embodiment the treatment system is a high-intensity focused ultrasound system.

In another embodiment the medical instrument comprises the high-intensity focused ultrasound system.

In another embodiment execution of the instructions further causes the processor to control the high-intensity focused ultrasound system to sonicate a target zone of a subject using the control data. The target zone may be or comprise multiple treatment cells. The treatment cells may also be referred to as sonication cells.

In another embodiment execution of the instructions enable the processor to modify the cell control data in response to the planning data and/or the treatment planning data during sonication of the target zone. This may also be interpreted as modifying the planning data and/or the treatment plan data during sonication of a particular sonication cell.

In another embodiment execution of the instructions further causes the processor to superimpose an ultrasound path indicative of the path of ultrasound from the high-intensity focused ultrasound system to the target zone on the physician graphical user interface. For instance the instructions may access a model or data which is descriptive of the ultrasound path from the ultrasound system to the target zone and superimpose it on the medical image. This may be useful because the operator of the physician graphical user interface may be able to easily see the path that ultrasound may take and thereby easily be able to take corrective actions to avoid ultrasound or too large amounts of ultrasound passing through critical points in a subject's anatomy.

In another embodiment the treatment system is a robotic treatment system. For example the robotic treatment system may be a system which uses a needle for intervention within a subject or as part of its function may control an endoscopic tool for inspecting the subject. This may be beneficial because the two separate displays may be used for planning and controlling the robotic treatment system.

In another embodiment the medical instrument further comprises a magnetic resonance imaging system for acquiring magnetic resonance imaging data from an imaging zone. Execution of the instructions further causes the processor to control the magnetic resonance imaging system to acquire the medical image. Execution of the instructions further causes the processor to repeatedly acquire thermal magnetic resonance data during sonication of the target zone. Execution of the instructions further causes the processor to repeatedly reconstruct a thermal magnetic resonance image using the thermal magnetic resonance data. The thermal magnetic resonance image may for instance be a temperature map or it may be an accumulated temperature dose. Execution of the instructions further causes the processor to repeatedly superimpose the thermal magnetic resonance image on the medical image using the physician graphical user interface and the technician graphical user interface.

In another embodiment the medical instrument further comprises a medical imaging system for acquiring the medical image. Execution of the instructions further causes the processor to control the medical imaging system to acquire the medical image.

In another embodiment the medical instrument is any one of the following: a computer tomography system or CT system, a diagnostic ultrasound system, and a magnetic resonance imaging system.

In another embodiment execution of the instructions further cause the processor to repeatedly acquire the medical image using the medical imaging system. Execution of the instructions further causes the processor to repeatedly update the medical image on the physician graphical user interface and the technician graphical user interface.

In another embodiment the planning data is descriptive of a boundary in the medical image. Execution of the instructions further causes the processor to display the boundary in the medical image on the technician graphical user interface.

In another embodiment the medical instrument further comprises a tablet computer. The tablet computer comprises the physician graphical user interface. The tablet computer may for instance be a tablet computer, it may also be a mobile communication device such as a smart phone. The tablet computer may connect to the processor via a variety of different protocols. For instance a wireless LAN or even a cellular communication protocol such as the GSM or G3 standard may be used.

In another embodiment the control data is generated in intervals not exceeding any one of the following: 10 minutes, 5 minutes, 2 minutes, 1 minute, 30 seconds, 5 seconds and 1 second.

In another aspect the invention provides for a computer program product comprising machine-executable instructions for execution by a processor controlling a medical instrument. The medical instrument comprises a first display device. The medical instrument further comprises a second display device. The medical instrument further comprises a database. Execution of the instructions causes the processor to receive a medical image. Execution of the instructions further cause the processor to display the medical image in a physician graphical user interface using the first display device. Execution of the instructions further cause the processor to display the medical image on a technician graphical user interface using the second display device.

Execution of the instructions further causes the processor to repeatedly receive planning data from the physician graphical user interface. The planning data is descriptive of the location in the medical image. Execution of the instructions further cause the processor to repeatedly display the planning data on the technician graphical user interface. Execution of the instructions further causes the processor to repeatedly receive treatment planning data from the technician graphical user interface. Execution of the instructions further cause the processor to repeatedly store the treatment plan data in the database. Execution of the instructions further cause the processor to repeatedly generate control data for controlling a treatment system using the treatment plan data in the database.

In another aspect the invention provides for a method of operating a medical instrument. The medical instrument comprises a medical instrument comprising a first display device and a second display device. The medical instrument further comprises a database. The method comprises the step of receiving a medical image. The method further comprises the step of displaying the medical image in a physician graphical user interface using the first display device. The method further comprises the step of displaying the medical image on the technician graphical user interface using the second display device. The method further comprises the step of repeatedly receiving planning data from the physician graphical user interface. The planning data is descriptive of a location in the medical image. The method further comprises the step of repeatedly displaying the planning data on the technician graphical user interface. The method further comprises the step of repeatedly receiving treatment plan data from the technician graphical user interface. The method further comprises the step of repeatedly storing the treatment plan data in the database. The method further comprises the step of repeatedly generating control data for controlling a treatment system using the treatment plan data in the database.

It is understood that one or more of the aforementioned embodiments of the invention may be combined as long as the combined embodiments are not mutually exclusive.

BRIEF DESCRIPTION OF THE DRAWINGS

In the following preferred embodiments of the invention will be described, by way of example only, and with reference to the drawings in which.

DETAILED DESCRIPTION OF THE EMBODIMENTS

Like numbered elements in these figures are either equivalent elements or perform the same function. Elements which have been discussed previously will not necessarily be discussed in later figures if the function is equivalent.

Figure 1:
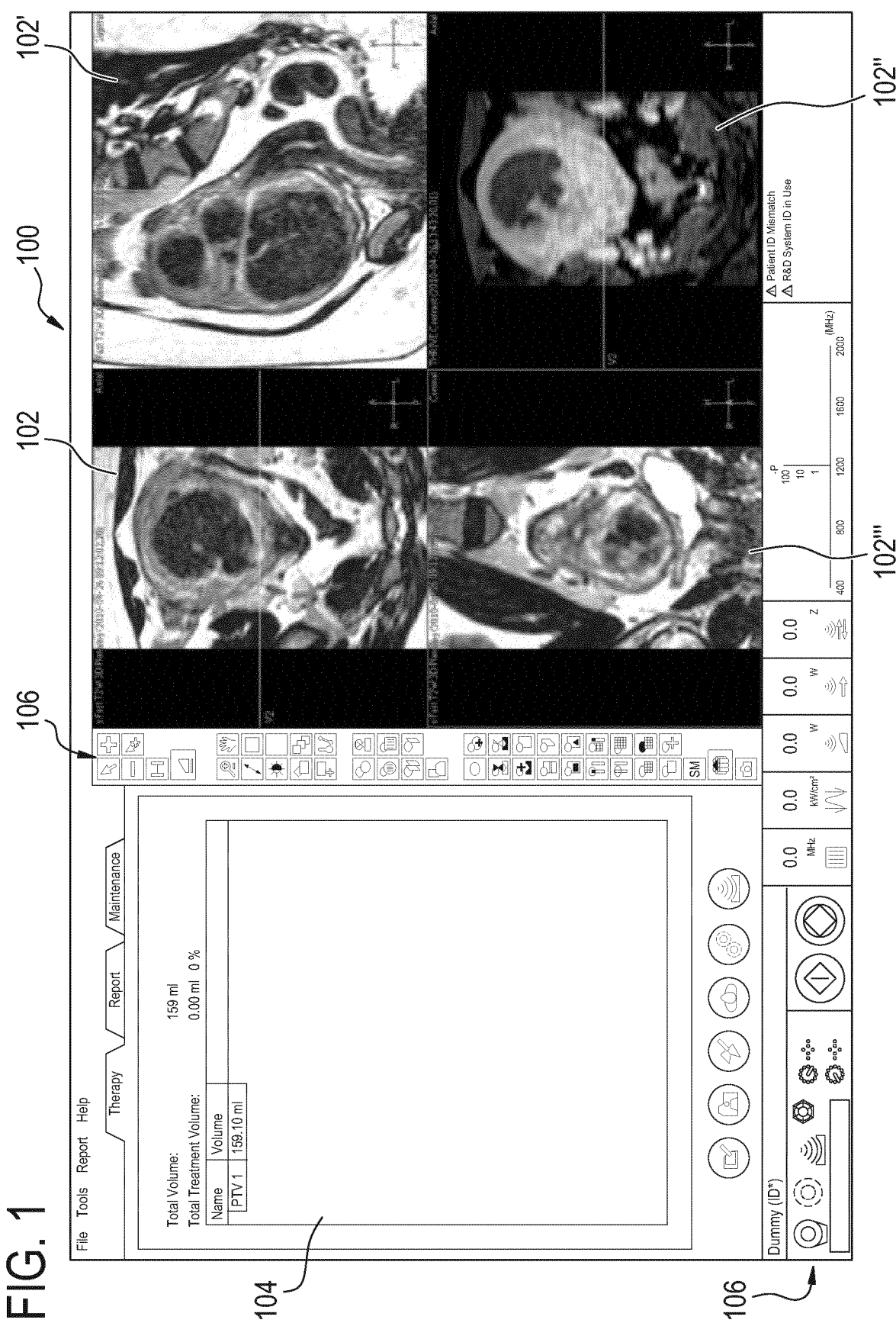
FIG. 1 shows an example of a technician graphical user interface.

FIG. 1 shows an example of a technician graphical user interface 100. The technician graphical user interface 100 shows a variety of medical images 102, 102', 102", 102'". These four images are magnetic resonance images 102, 102', 102", 102'" and show different slices of the same region and are used for planning a high-intensity focused ultrasound sonication. There is a region 104 which displays information 104 relevant to the planned sonication. There are several regions 106 which contain tools for planning the sonication of the subject.

Figure 2:
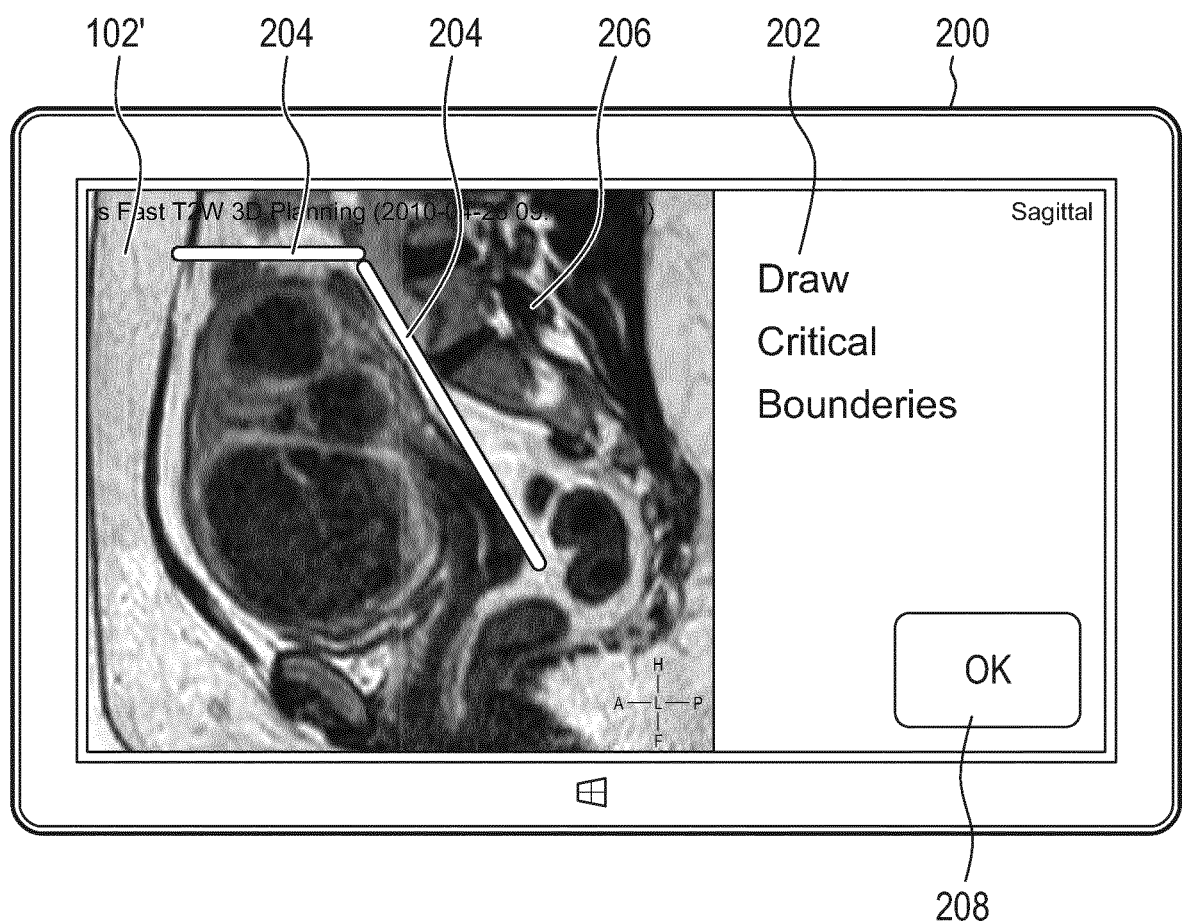
FIG. 2 shows an example of a physician graphical user interface.

FIG. 2 shows a first display device 200. In this case the first display device 200 is a tablet computer. The first display device 200 has a physician graphical user interface 202. The physician graphical user interface 202 displays the medical image 102'. On this image an operator or user uses the graphical user interface 202 to input two line segments 204. The two line segments 204 are used to indicate a sensitive region 206 which should not be sonicated. The graphical user interface 202 is also shown as having a button 208 which can be used to accept the input of the line segments 204. After the button 208 is pushed this information is sent to the technician graphical user interface 100.

Figure 3:
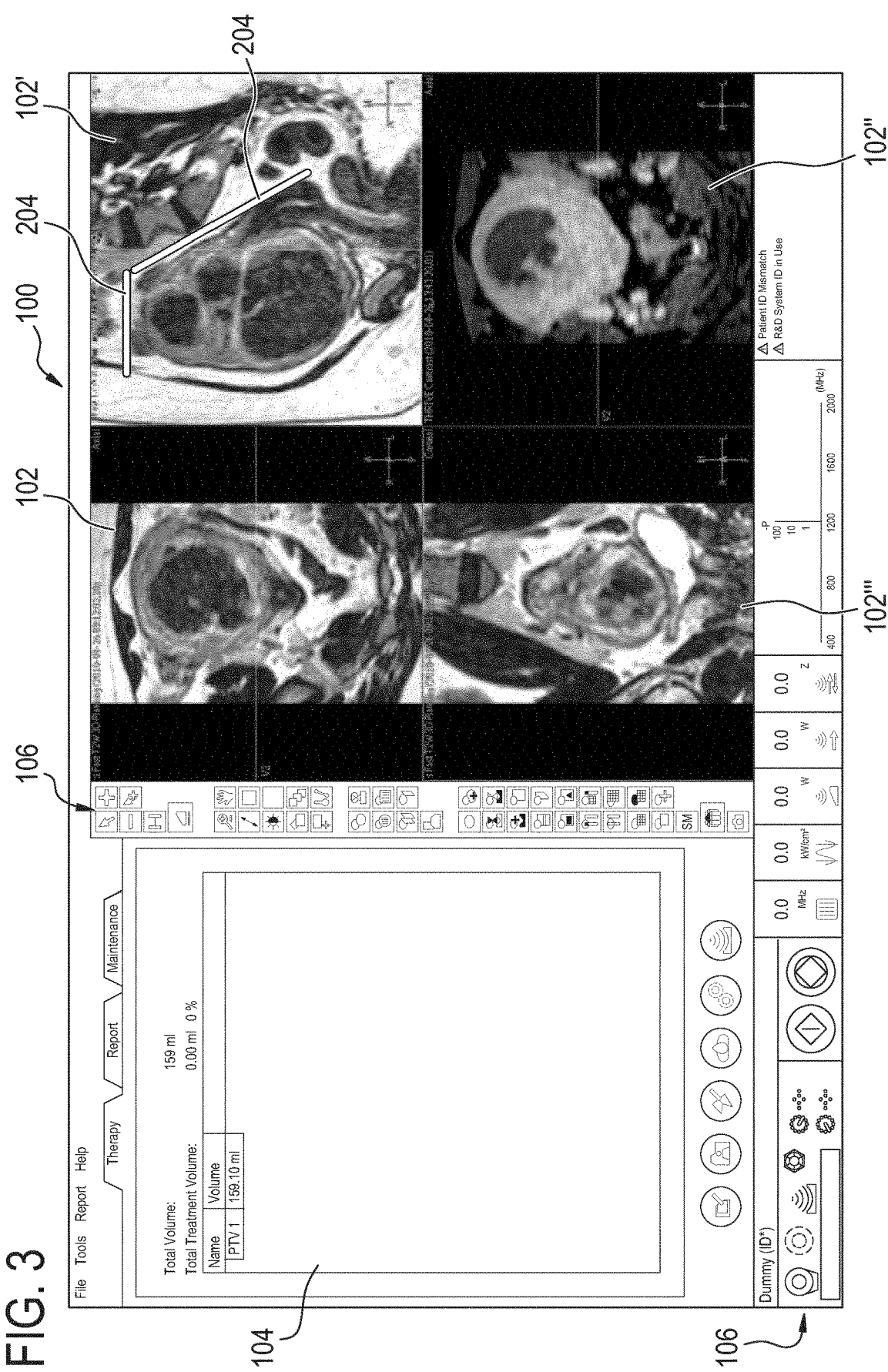
FIG. 3 shows a further example of a technician graphical user interface.

FIG. 3 shows the same graphical user interface 100 after the line segments 204 have been sent to the technician graphical user interface 100. The line segments 204 are displayed on the medical image 102'.

Figure 4:
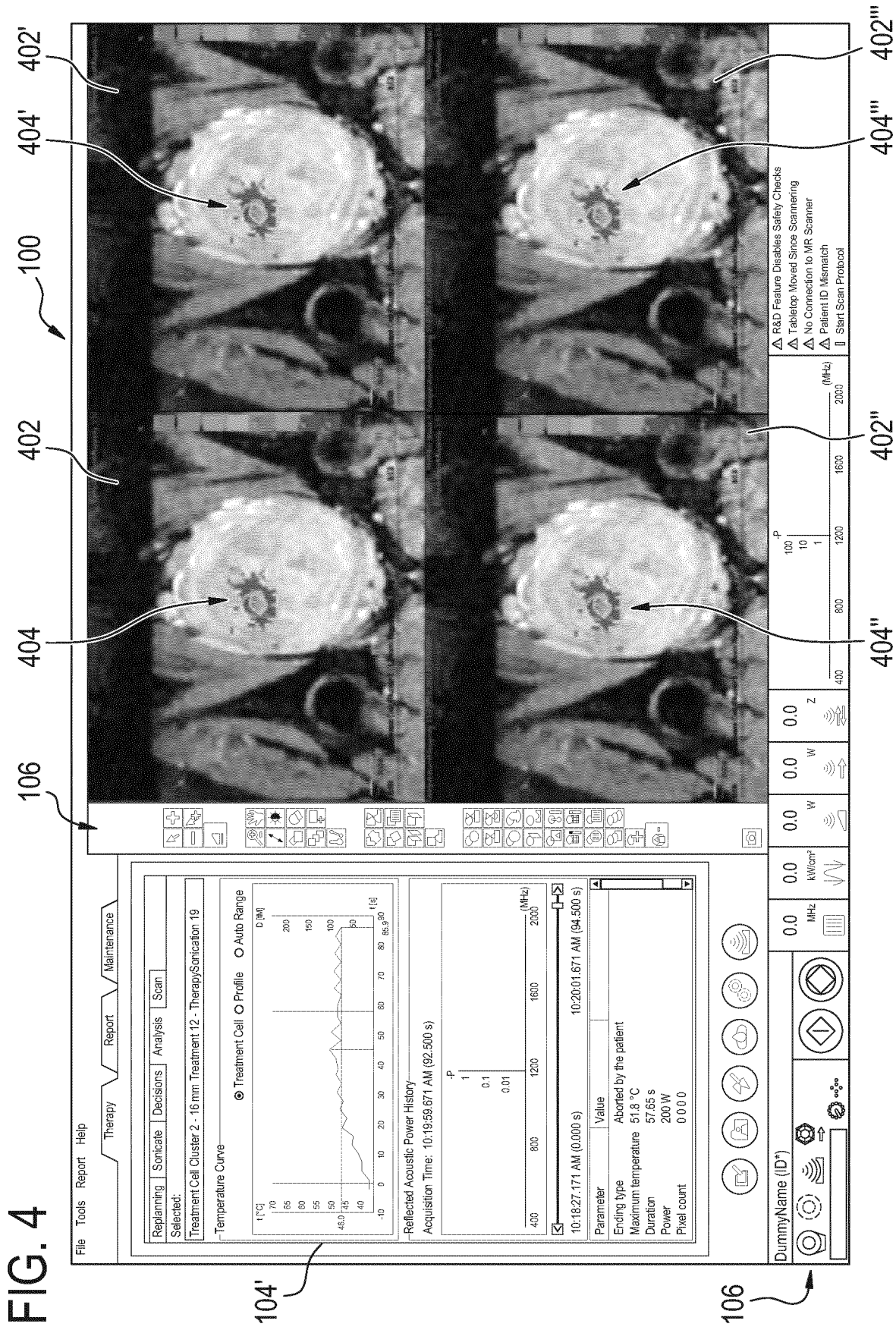
FIG. 4 shows a further example of a technician graphical user interface.

FIG. 4 shows a further example of the technician graphical user interface 100. In this example four new medical images 402, 402', 402", and 402'" are displayed. Each medical image 402, 402', 402", 402'" also displays temperature data 404, 404', 404", 404'". Temperature data 404 is superimposed on image 402. Temperature data 404' is superimposed on image 402'. Temperature data 404" is superimposed on image 402". Temperature data 404'" is superimposed on image 402'". The region 104' displays a summary of data related to the temperature data 404, 404', 404", 404'".

Figure 5:
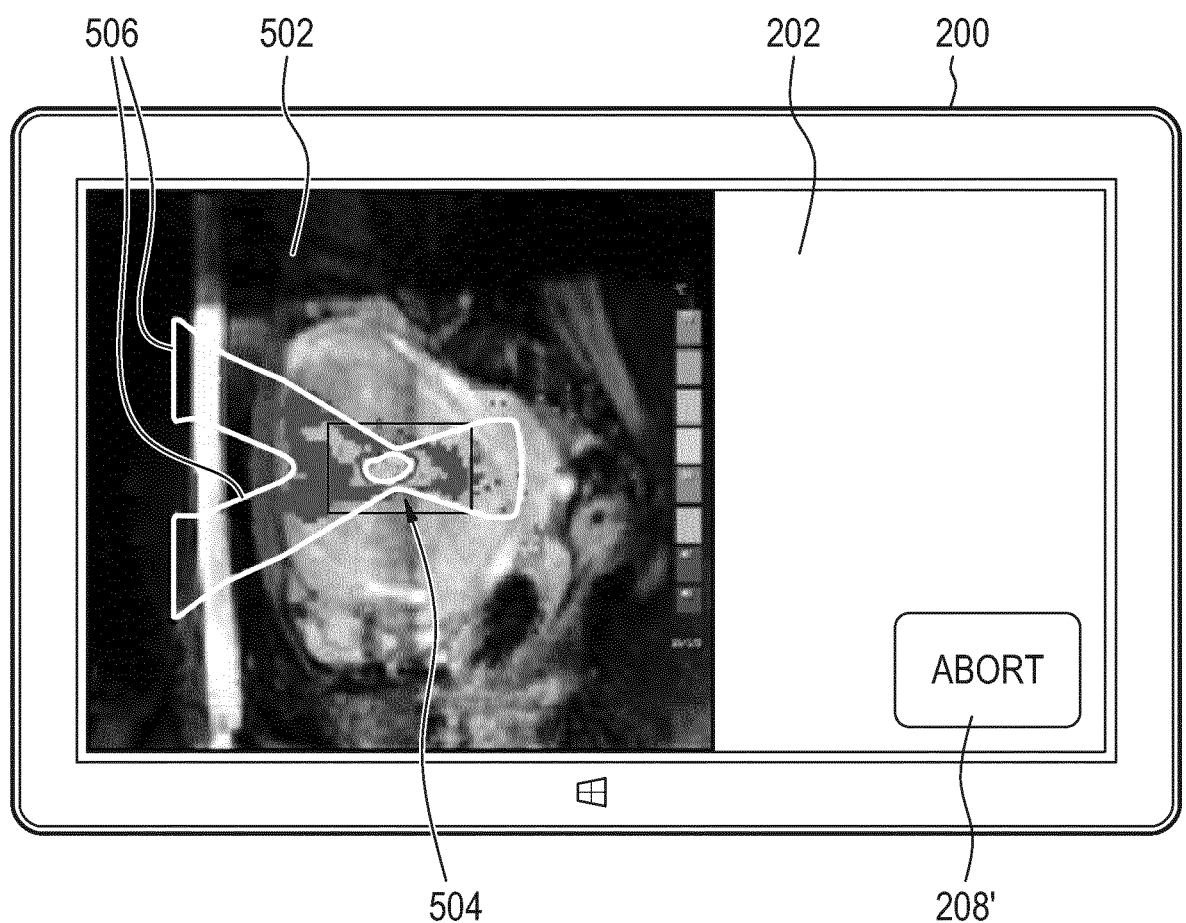
FIG. 5 shows a further example of a physician graphical user interface.

FIG. 5 shows a further view of the first display device 200. The first display device 200 shows a modified version of the user interface 202. A different medical image 502 is displayed. Superimposed on the medical image 502 is temperature data 504. Also displayed on the medical image 502 is a line indicating the path 506 of ultrasound from the high-intensity focused ultrasound system to a target zone. The physician has a button 208' on the user interface 208 which enables the operator to abort the sonication of the subject. FIG. 4 shows a technician's view on a main display and focuses on the overall heating and system performance. FIG. 5 illustrates the physician's graphical user interface 202 and focuses on other areas of clinical interest such as where the ultrasound is going relative to the subject's anatomy.

Figure 6:
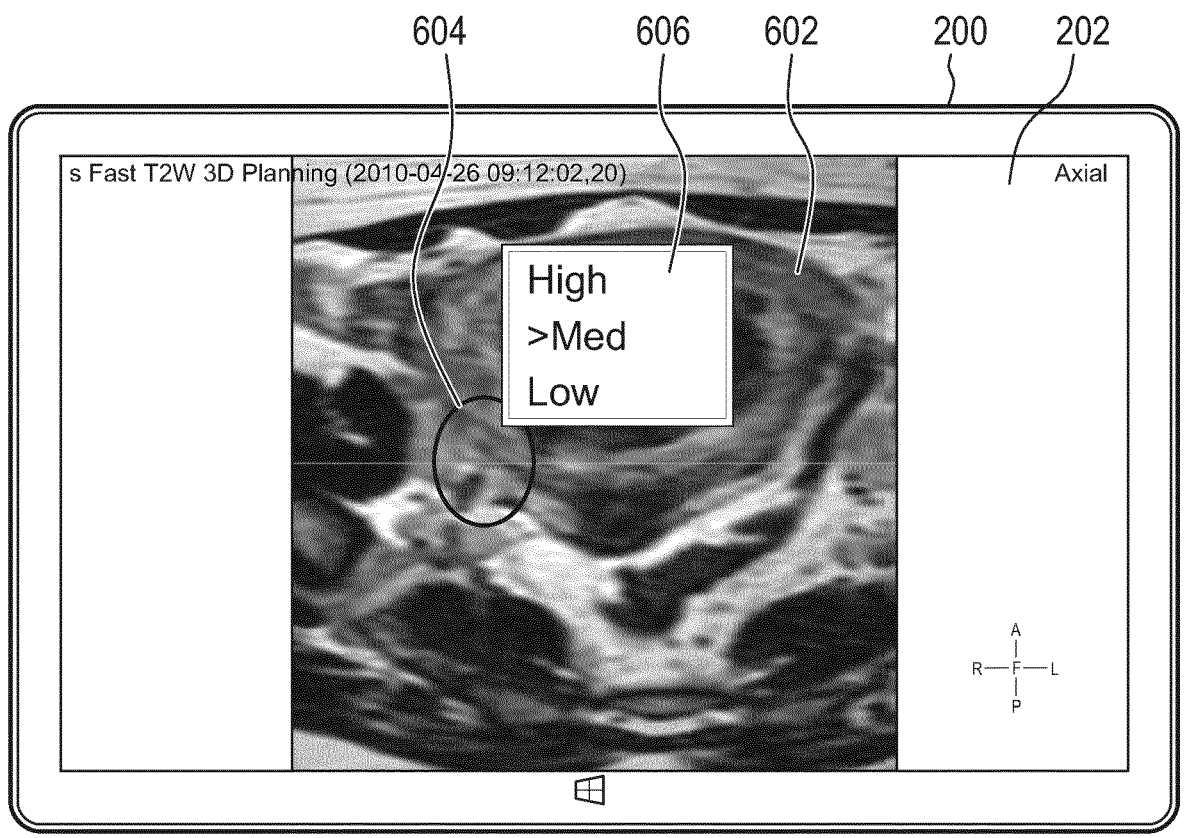
FIG. 6 shows a further example of a physician graphical user interface.

FIG. 6 shows a further view of the first display device 200. In this example the physician graphical user interface 202 displays a different medical image 602. Indicated on the medical image 602 is a sonication cell 604. By tapping on the sonication cell 604 a menu 606 is opened. This menu enables the operator to select an energy dose delivered to the cell.

Figure 7:
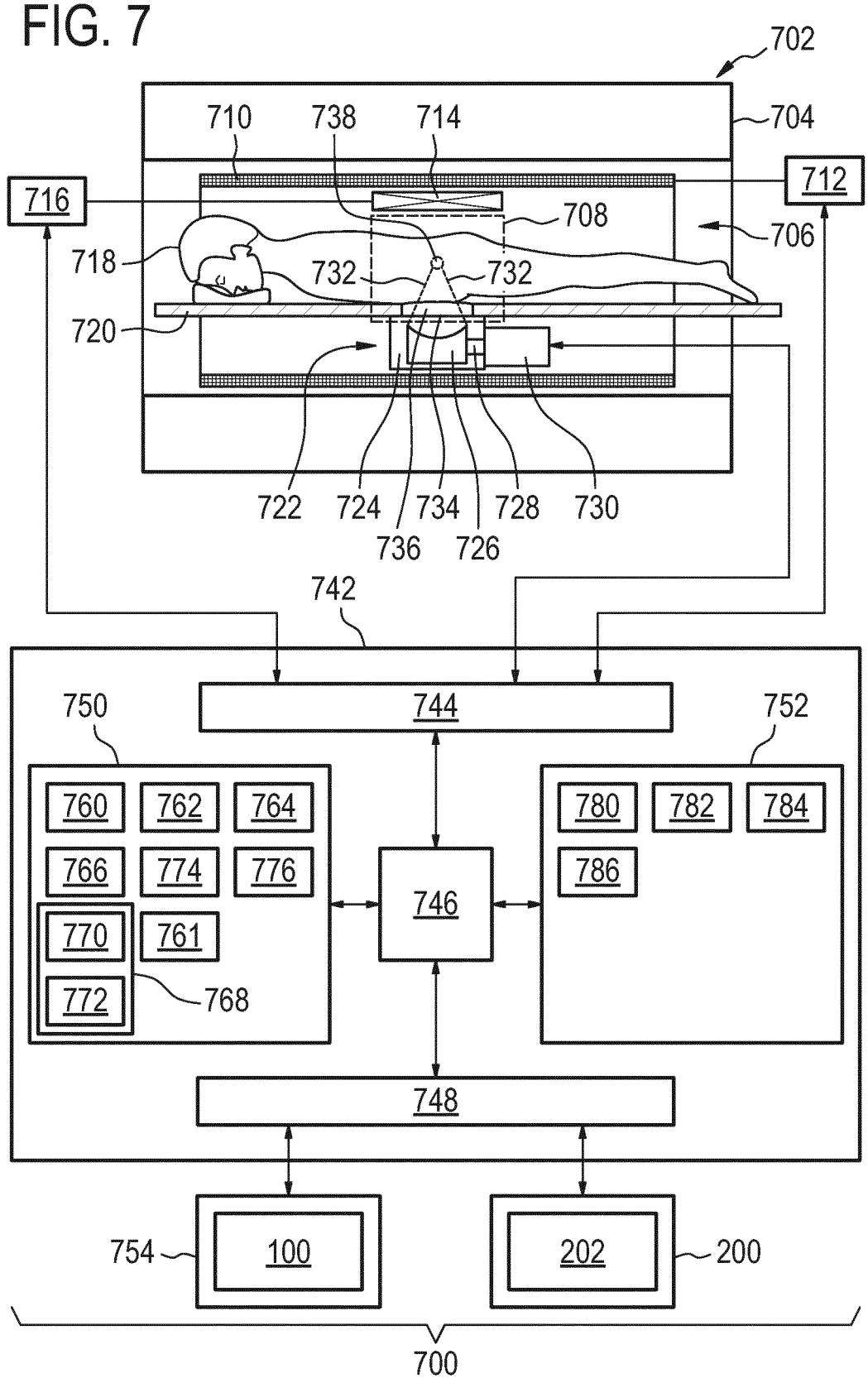
FIG. 7 shows an example of a medical instrument.

FIG. 7 shows an example of a medical instrument 700. The medical instrument 700 comprises a magnetic resonance imaging system 702. The magnetic resonance imaging system comprises a magnet 704. The magnet 704 is a cylindrical type superconducting magnet with a bore 706 through the center of it. The magnet has a liquid helium cooled cryostat with superconducting coils. It is also possible to use permanent or resistive magnets. The use of different types of magnets is also possible for instance it is also possible to use both a split cylindrical magnet and a so called open magnet. A split cylindrical magnet is similar to a standard cylindrical magnet, except that the cryostat has been split into two sections to allow access to the iso-plane of the magnet, such magnets may for instance be used in conjunction with charged particle beam therapy. An open magnet has two magnet sections, one above the other with a space in-between that is large enough to receive a subject: the arrangement of the two sections area similar to that of a Helmholtz coil. Open magnets are popular, because the subject is less confined. Inside the cryostat of the cylindrical magnet there is a collection of superconducting coils. Within the bore 706 of the cylindrical magnet there is an imaging zone 708 where the magnetic field is strong and uniform enough to perform magnetic resonance imaging.

Within the bore 706 of the magnet there is also a set of magnetic field gradient coils 710 which are used for acquisition of magnetic resonance data to spatially encode magnetic spins within the imaging zone 708 of the magnet 704. The magnetic field gradient coils are connected to a magnetic field gradient coil power supply 712. The magnetic field gradient coils 710 are intended to be representative. Typically magnetic field gradient coils contain three separate sets of coils for spatially encoding in three orthogonal spatial directions. A magnetic field gradient power supply 712 supplies current to the magnetic field gradient coils 710. The current supplied to the magnetic field coils is controlled as a function of time and may be ramped or pulsed.

Adjacent to the imaging zone 708 is a radio-frequency coil 714 for manipulating the orientations of magnetic spins within the imaging zone 708 and for receiving radio transmissions from spins also within the imaging zone. The radio-frequency coil may contain multiple coil elements. The radio-frequency coil may also be referred to as a channel or an antenna. The radio-frequency coil 714 is connected to a radio frequency transceiver 716. The radio-frequency coil 714 and radio frequency transceiver 716 may be replaced by separate transmit and receive coils and a separate transmitter and receiver. It is understood that the radio-frequency coil 714 and the radio-frequency transceiver 716 are representative. The radio-frequency coil 714 is intended to also represent a dedicated transmit antenna and a dedicated receive antenna. Likewise the transceiver 716 may also represent a separate transmitter and receivers.

A subject 718 is shown as reposing on a subject support 720 and is located partially within the imaging zone 708. The example shown in FIG. 7 comprises a high-intensity focused ultrasound system 722. The high-intensity focused ultrasound system comprises a fluid-filled chamber 724. Within the fluid-filled chamber 724 is an ultrasound transducer 726. Although it is not shown in this figure the ultrasound transducer 726 may comprise multiple ultrasound transducer elements each capable of generating an individual beam of ultrasound. This may be used to steer the location of a sonication point 738 electronically by controlling the phase and/or amplitude of alternating electrical current supplied to each of the ultrasound transducer elements.

The ultrasound transducer 726 is connected to a mechanism 728 which allows the ultrasound transducer 726 to be repositioned mechanically. The mechanism 728 is connected to a mechanical actuator 730 which is adapted for actuating the mechanism 728. The mechanical actuator 730 also represents a power supply for supplying electrical power to the ultrasound transducer 726. In some embodiments the power supply may control the phase and/or amplitude of electrical power to individual ultrasound transducer elements. In some embodiments the mechanical actuator/power supply 730 is located outside of the bore 706 of the magnet 704.

The ultrasound transducer 726 generates ultrasound which is shown as following the path 732. The ultrasound 732 goes through the fluid-filled chamber 728 and through an ultrasound window 734. In this embodiment the ultrasound then passes through a gel pad 736. The gel pad 736 is not necessarily present in all embodiments but in this embodiment there is a recess in the subject support 720 for receiving a gel pad 736. The gel pad 736 helps couple ultrasonic power between the transducer 726 and the subject 718. After passing through the gel pad 736 the ultrasound 732 passes through the subject 718 and is focused to a sonication point 738. The sonication point 738 may be moved through a combination of mechanically positioning the ultrasonic transducer 726 and electronically steering the position of the sonication point 738.

The magnetic field gradient coil power supply 712, the transceiver 716, and the mechanical actuator/power supply 730 of the high-intensity focused ultrasound system 722 are shown as being connected to a hardware interface 744 of computer 742. The computer 742 further comprises a processor 746, a user interface 748, computer storage 750, and computer memory 752. The hardware interface 744 enables the processor 746 to send and receive commands and data in order to control the functioning of the medical instrument 700. The processor 746 is further connected to the user interface 748, the computer storage 750, and the computer memory 752.

The user interface 748 is shown as being connected to a second display device 754 and a first display device 200. The second display device 754 has a technician graphical user interface 100 and the second display device has a physician graphical display device 202. The depiction of the second display device 754 and the first display device 200 is representative. These display devices 754, 200 may be a part of the computer system 742 or they may be separate computers themselves. In particular the first display device 200 may in some examples be a tablet computer.

The computer storage 750 is shown as containing a pulse sequence 760 which may be used by the magnetic resonance imaging system 702 to acquire magnetic resonance data 761. The computer storage 750 is shown as further containing a magnetic resonance image 762. The magnetic resonance image 762 is equivalent to the magnetic resonance images shown in FIGS. 1-6. The computer storage 750 is shown as further containing planning data 764 received from the physician graphical user interface 202. The computer storage 750 is shown as further containing treatment plan data 766 that was received from the technician graphical user interface 100.

The computer storage 750 is shown as further containing a database 768. The database 768 contains control data 770, 772 for controlling the operation of the high-intensity focused ultrasound system 722 to sonicate the subject 718. The sonication regions are divided into treatment cells or sonication cells. The control data 770, 772 in the database 768 is stored independently for each sonication or treatment cell. The database 768 may for example be a relational database with transaction control. This enables the two separate user interfaces 100, 202 to independently modify data within the database 768 without interfering with the other's work. The computer storage 750 is shown as further containing thermal magnetic resonance data 774. This is an optional example of what may be acquired with the magnetic resonance imaging system 702. For instance the pulse sequence 760 could be adapted to acquire the thermal magnetic resonance data and/or the magnetic resonance data. The computer storage 750 is shown as containing a thermal map 776 reconstructed from the thermal magnetic resonance data 774. The thermal map 776 may for instance be used to calculate a thermal dose and/or to display temperature data on the two graphical user interfaces 100, 202.

The computer memory 752 is shown as containing a control module 780. The control module 780 contains computer-executable code which enables the processor 746 to control the operation and function of the medical instrument 700. The computer memory 752 is further shown as containing an image reconstruction module 782. The image reconstruction module 782 enables the processor 746 to reconstruct the thermal map 776 from the thermal magnetic resonance data 774 and/or to reconstruct the magnetic resonance image 762 from the magnetic resonance data 761. The computer memory 752 is further shown as containing the control data generation module 784 which was used to generate the control data 770, 772 using input from the graphical user interfaces 100, 202.

The computer memory 752 is further shown as containing a query engine and a transaction manager 786. The query engine and transaction manager 786 contains computer-executable code for the processor 746 to interact with the database 768 to add, modify, and/or remove data from the database 768. If the database 768 is a relational database then the query engine and transaction manager may manage the function of enabling only the technician graphical user interface 100 or the physician graphical user interface 202 to modify the data for a particular treatment or sonication cell.

In this example a magnetic resonance imaging system 702 is shown. This is however representative in other medical imaging techniques such as computer tomography or diagnostic ultrasound may be used in its place to acquire the medical image. In some examples the medical instrument only comprises the computer 742 and the two display devices 754, 200.

Figure 8:
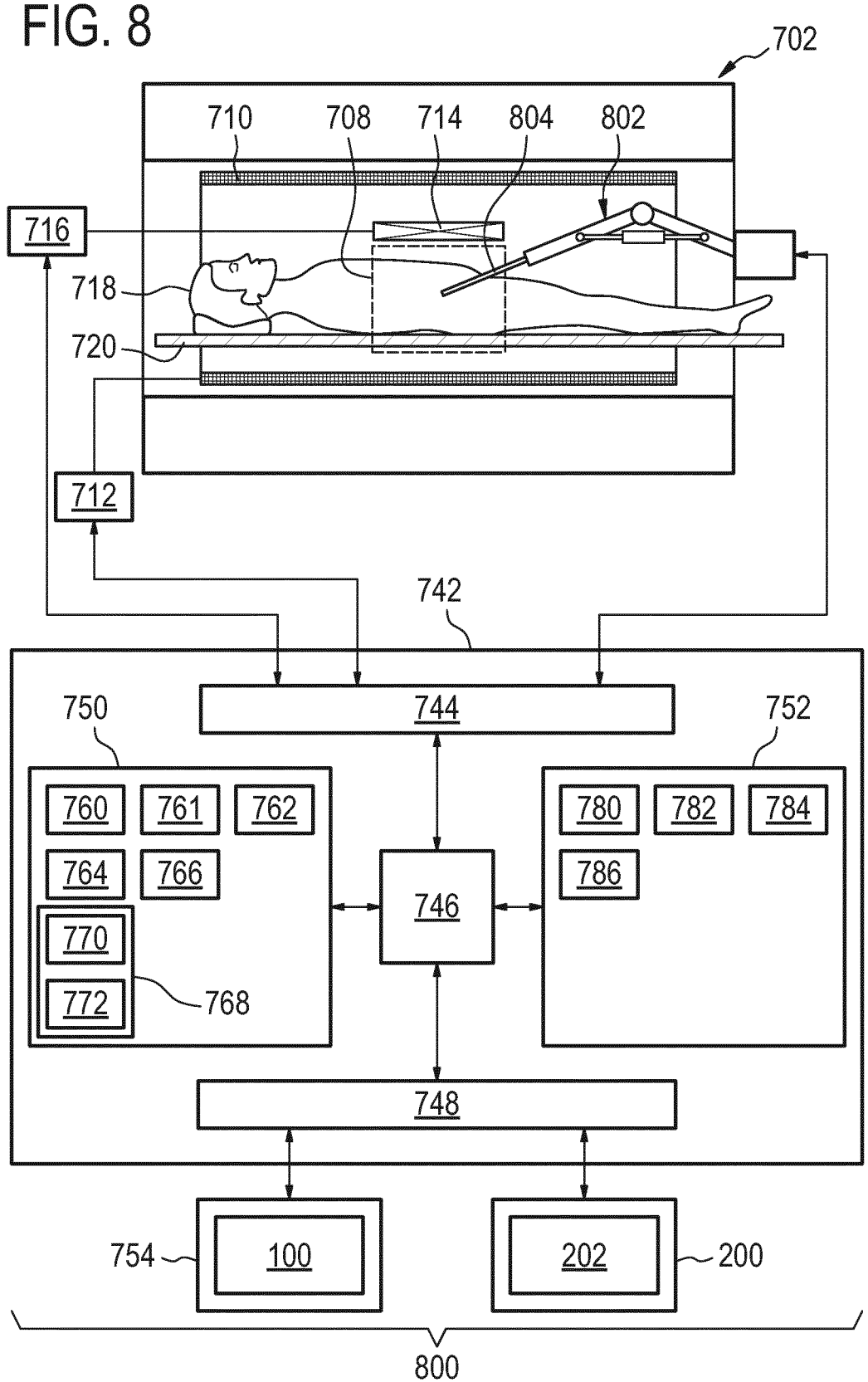
FIG. 8 shows a further example of a medical instrument.

FIG. 8 shows a further example of a medical instrument 800. The medical instrument 800 shown in FIG. 8 is similar to the medical instrument 700 shown in FIG. 7. However, the high-intensity focused ultrasound system 722 of FIG. 7 has been replaced with a robotic treatment system 802. The robotic treatment system 802 is shown as having a needle 804 which can be inserted into the subject 718. The movement and the progress of the needle 804 is controlled by designating treatment cells also. In this way the control methodology and the method of controlling the system using the database 768 is equivalent. The robotic treatment system 802 is shown as being connected to the hardware interface 744 such that the processor 746 can control the operation and function of the robotic treatment system 802 using the control data 770, 772.

Figure 9:
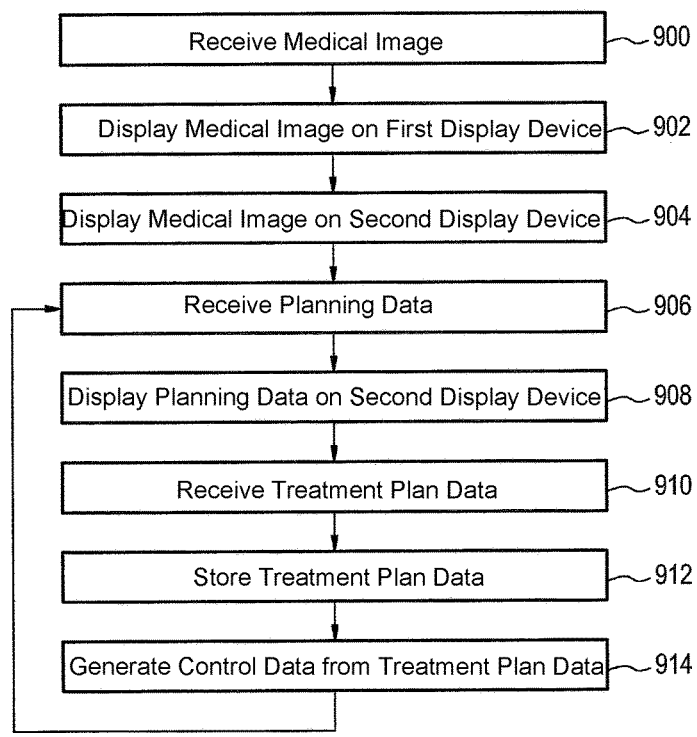
FIG. 9 shows a flow chart illustrating an example of a method.

FIG. 9 shows a flowchart which illustrates an example of a method. In step 900 a medical image is received. In some examples the medical image may be acquired using a medical imaging system such as a magnetic resonance imaging system. Next in step 902 the medical image is displayed on a physician graphical user interface of a first display device. Next in step 904 the medical image is displayed on a technician graphical user interface of a second display device. In this example the steps 900, 902 and 904 are shown as only being performed once. However, in some examples the medical image may be acquired periodically or more than once. In this case it is possible that the method may be changed to update the medical image displayed on the physician graphical user interface and the technician graphical user interface. Next in step 906 planning data is received from the physician graphical user interface. The planning data is descriptive of the location in the medical image. Next in step 908 the planning data is displayed on the technician graphical user interface. Next in step 910 treatment plan data is received from the technician graphical user interface. Then in step 912 the treatment plan data is stored in a database. Then finally in step 914 control data is generated for controlling the treatment system using the treatment plan data in the database. This method is then performed in a loop where the method returns to step 906. This is representative of the physician graphical user interface and the technician graphical user interface being used repeatedly during the process of controlling the treatment system.

This invention describes a method where the interactive therapy control graphical user interface is divided on multiple display and control devices to allow concurrent therapy control and planning with a shared data model.

In HIFU therapy, the treatment is often iterative and interactive process, where the treatment cell positions need to be defined during the therapy, based on the tissue response and inadvertent patient movement. Normally the interactive modifications are carried out with a keyboard and mouse by a technician, under the voice guidance of the physician.

Here we propose an example method where the technician continues to use the large screen display(s)+ mouse and keyboard for the overall control and for tasks needing accurate graphical object manipulation or lengthy textual entries. However, the physician can also be equipped with an input device, such as a pad-computer with touch screen.

The treatment of an individual cell is rather lengthy procedure during sonication, typically tens of seconds. During the treatment, the heating needs to be closely monitored to prevent unwanted heating. The monitoring can be improved if the technician and physician can concentrate on different aspects of the heating and inadvertent events.

For sonications that do not need intervention or input from the physician, the physician can concentrate to further develop the treatment plan by selecting the energy doses and treatment cell positions and sizes for subsequent sonications. These kinds of operations can also be carried out while the technician is preparing the system for sonications or performing lengthy hardware control. This decreases the total duration of the operation and improves the accuracy and quality of the treatment as treatment cell positions can be altered by the physicist and the physicist can browse the images without relying on the technician.

Separate peripherals or control interfaces are provided for additional operators of the system. Displays can either be provided by the workstation, by supporting multiple display and control devices, or the displays can actually be separate computers with their own display and controls, where the separate computers communicate with a common server (typically the workstation).

In one example, the separate display provides interactive viewing capabilities, allowing the operator to control his own view into the treatment. For example, during a sonication, the operator can view the near-field heating effects, while the technician is monitoring the energy dose on top of the treatment cell. The operator can use a touch screen to pan, zoom, and window the image data—or, if several slices are provided, select between the slices.

In another example, the separate display provides controls for modifying common data that is shared with the other users of the system. For example, the operator can add treatment cells to the treatment plan. The modifications are automatically made visible for the other users. Business logic rules take care of preventing disruptive or confusing data modifications and suppress similar modification results, depending on the system state. For example, during sonication, treatment cell addition notifications are not to be displayed while the technician is concentrating on heating the target volume. Other uses for the controls can be graphical or textual annotation and reporting of the treatment—the peripheral can also contain voice recording devices. The graphical or textual annotations can also be used to guide the technician to position regions of interest, planned target volumes, or treatment cells once the technician becomes available from his/her current task. For example, the physician can highlight the distances to critical structures or correct auto-segmented structures so that the technician can fix or add treatment cells in his/her current plan.

An example use is to provide a workstation with two displays. One display is the standard display used by the technician. The other display can be a touch screen for the physician. The touch screen can display a Windows Metro-application for displaying and browsing of the images with gestures, E.g., pinching motion for zooming/shrinking.

Another example is to use a workstation with a separate touch screen tablet device. The workstation with the standard display is used by the technician. The touch screen tablet device is used by the physician. The touch screen table device runs an application for displaying and browsing of the images with gestures, and allows addition and movement of treatment cells in the therapy plan.

Figure 10:
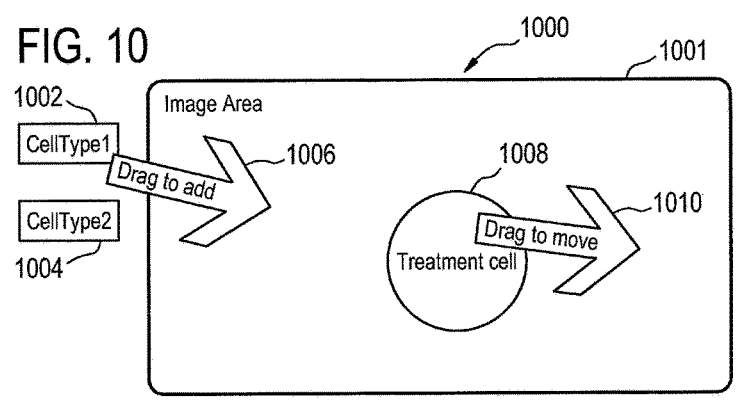
FIG. 10 shows an example of a graphical user interface.

For example, FIG. 10 shows a user interface 1000. The user interface has an imaging area 1001. A button 1002 enables the selection of a first type of treatment or sonication cell. A second button 1004 enables the selection of a second type of treatment or sonication cell. A cell can be added by clicking 1002 or 1004 and then dragging 1006 the cell to the desired location. Alternatively, an existing cell 1008 can be dragged 1010 to a new location.

Due to concurrent use of data, the underlying common data structures are made thread safe on the serving workstation. To also support concurrent modifications to complex data sets, modifications to the datasets are transacted. If conflicts occur due to concurrent data modifications to same data elements, the modifications are rolled back and the operation reattempted or cancelled—if the concurrent modification can lead to ambiguous data or safety-related data is being edited, the operation is cancelled and indicated to the user with visual/sound cues (e.g., graphics snap-in to the original position when a graphical movement operation for a treatment cell was attempted while the other operator was modifying the treatment cell energy dose on the treatment cell to be moved).

While the invention has been illustrated and described in detail in the drawings and foregoing description, such illustration and description are to be considered illustrative or exemplary and not restrictive; the invention is not limited to the disclosed embodiments.

Other variations to the disclosed embodiments can be understood and effected by those skilled in the art in practicing the claimed invention, from a study of the drawings, the disclosure, and the appended claims. In the claims, the word "comprising" does not exclude other elements or steps, and the indefinite article "a" or "an" does not exclude a plurality. A single processor or other unit may fulfill the functions of several items recited in the claims. The mere fact that certain measures are recited in mutually different dependent claims does not indicate that a combination of these measured cannot be used to advantage. A computer program may be stored/distributed on a suitable medium, such as an optical storage medium or a solid-state medium supplied together with or as part of other hardware, but may also be distributed in other forms, such as via the Internet or other wired or wireless telecommunication systems. Any reference signs in the claims should not be construed as limiting the scope.

LIST OF REFERENCE NUMERALS 100 technician graphical user interface
102 medical image
102' medical image
102" medical image
102''' medical image
104 data display
104' data display
106 controls
200 first display device
202 physician graphical user interface
204 line segment
206 sensitive region
208 control button
402 medical image 402' medical image
402" medical image
402"' medical image
404 temperature data
404' temperature data
404" temperature data
404"' temperature data
502 medical image
504 temperature data
506 path of ultrasound
602 medical image
604 sonication cell
606 menu
700 medical instrument
702 magnetic resonance imaging system
704 magnet
706 bore of magnet
708 imaging zone
710 magnetic field gradient coils
712 magnetic field gradient coils power supply
714 radio-frequency coil
716 transceiver
718 subject
720 subject support
722 high intensity focused ultrasound system
724 fluid filled chamber
726 ultrasound transducer
728 mechanism
730 mechanical actuator/power supply
732 path of ultrasound
734 ultrasound window
736 gel pad
738 sonication point
742 computer system
744 hardware interface
746 processor
748 user interface
750 computer storage
752 computer memory
754 second display device
760 pulse sequence
761 magnetic resonance data
762 magnetic resonance image
764 planning data
766 treatment plan data
768 database
770 control data for first treatment cell
772 control data for second treatment cell
774 thermal magnetic resonance data
776 thermal map
780 control module
782 image reconstruction module
784 control data generation module
786 query engine and transaction manager
800 medical instrument
802 robotic treatment system
804 needle
1000 user interface
1001 image area
1002 button
1004 button
1006 drag cell to location
1008 existing cell
1010 drag existing cell to new location.

The invention claimed is:

1. A medical instrument comprising:
a first display device;
a second display device;
a database;
a memory for storing machine executable instructions;
a processor for an execution of the machine executable instructions,
wherein the execution of the machine executable instructions causes the processor to:
receive a medical image;
display the medical image on a physician graphical user interface using the first display device;
display the medical image on a technician graphical user interface using the second display device;
wherein the execution of the machine executable instructions causes the processor to repeatedly:
receive planning data from the physician graphical user interface, wherein the planning data is descriptive of a location in the medical image;
display the planning data on the technician graphical user interface;
receive treatment plan data from the technician graphical user interface;
store the treatment plan data in the database;
generate, using the treatment plan data in the database, treatment system control data for controlling a treatment system; and
wherein the execution of the machine executable instructions further causes the processor to modify the treatment system control data for controlling the treatment system by operations including: dividing at least a portion of the medical image into treatment cells,
dividing the treatment system control data with reference to each of the treatment cells,
wherein the treatment cells comprises a first treatment cell and a second treatment cell, and
wherein the divided treatment system control data comprises first treatment cell control data of the first treatment cell and second treatment cell control data of the second treatment cell;
receiving a selection of the first treatment cell,
wherein the selection of the first treatment cell is based on the treatment plan data;
locking the first treatment cell control data of the first treatment cell in the database to restrict modification of the first treatment cell control data to using only the treatment plan data;
modifying the first treatment cell control data using only the treatment plan data;
unlocking the first treatment cell control data after the modification of the first treatment cell control data;
after unlocking the first treatment cell control data, receiving a selection of the second treatment cell, wherein the selection of the second treatment cell is based on the planning data;
locking the second treatment cell control data in the database to limit modification of the second treatment cell control data to using only the planning data;
modifying, using only the planning data, the second treatment cell control data; and
unlocking the second treatment cell control data in the database;
wherein the locking and unlocking of the first treatment cell control data and the second treatment cell control data prevents the first treatment cell control data and the second treatment cell control data from being modified by the physician graphical user interface and the technician graphical user interface at the same time.

2. The medical instrument of claim 1, wherein the treatment system is a high intensity focused ultrasound system and the execution of the machine executable instructions further causes the processor to control the high intensity focused ultrasound system to sonicate a target zone of a subject using the treatment system control data.

3. The medical instrument of claim 2, wherein the execution of the machine executable instructions enables the processor to modify the first treatment cell control data in response to only the treatment plan data and to modify the second treatment cell control data in response to only the planning data during sonication of the target zone.

4. The medical instrument of claim 2, wherein the execution of the machine executable instructions causes the processor to superimpose an ultrasound path indicative of the path of ultrasound from the high intensity focused ultrasound system to the target zone on the physician graphical user interface.

5. The medical instrument of claim 2, wherein the medical instrument further comprises a magnetic resonance imaging system for acquiring magnetic resonance imaging data from an imaging zone, wherein the execution of the machine executable instructions further causes the processor to control the magnetic resonance imaging system to acquire the medical image, wherein the execution of the machine executable instructions further causes the processor to repeatedly:
acquire thermal magnetic resonance data during sonication of the target zone;
reconstruct a thermal magnetic resonance image using the thermal magnetic resonance data; and
superimpose the thermal magnetic resonance image on the medical image on the physician graphic user interface and the technician graphical user interface.

6. The medical instrument of claim 5, wherein the execution of the machine executable instructions further causes the processor to repeatedly:
acquire the medical image using the medical imaging system; and
update the medical image on the physician graphical user interface and the technician graphical user interface.

7. The medical instrument of claim 1, wherein the treatment system is a robotic treatment system.

8. The medical instrument of claim 1, wherein the medical instrument further comprises a medical imaging system for acquiring the medical image, and wherein the execution of the machine executable instructions further causes the processor to control the medical imaging system to acquire the medical image.

9. The medical instrument of claim 1, wherein the medical instrument is any one of the following: a computed tomography system, a diagnostic ultrasound system, and a magnetic resonance imaging system.

10. The medical instrument of claim 1, wherein the planning data is descriptive of a boundary in the medical image, wherein the execution of the machine executable instructions further causes the processor to display the boundary in the medical image on the technician graphical user interface.

11. The medical instrument of claim 1, wherein the medical instrument further comprises a tablet computer, wherein the tablet computer comprises the physician graphical user interface.

12. The medical instrument of claim 1, wherein the treatment system control data is generated in intervals not exceeding any one of the following: 10 minutes, 5 minutes, 2 minutes, 1 minute, 30 seconds, 5 seconds, and 1 second.

13. A non-transitory computer readable medium storing machine executable instructions for an execution by a processor controlling a medical instrument, wherein the medical instrument comprises a first display device, wherein the medical instrument further comprises a second display device, wherein the medical instrument further comprises a database, wherein the execution of the machine executable instructions causes the processor to:
receive a medical image;
display the medical image in a physician graphical user interface using the first display device;
display the medical image on a technician graphical user interface using the second display device;
wherein the execution of the machine executable instructions causes the processor to repeatedly:
receive planning data from the physician graphical user interface,
wherein the planning data is descriptive of a location in the medical image;
display the planning data on the technician graphical user interface;
receive treatment plan data from the technician graphical user interface;
store the treatment plan data in the database;
generate, using the treatment plan data in the database, treatment system control data for controlling a treatment system; and
modifying the treatment system control data by operations including:
dividing at least a portion of the medical image into treatment cells,
dividing the treatment system control data with reference to each of the treatment cells,
wherein the treatment cells comprises a first treatment cell and a second treatment cell,
wherein the divided treatment system control data comprises first treatment cell control data of the first treatment cell and second treatment cell control data of the second treatment cell, and
wherein the database stores the first treatment system control data and the second treatment system control data;
receiving a selection of the first treatment cell, wherein the selection of the first treatment cell is based on the treatment plan data;
locking the first treatment cell control data of the first treatment cell in the database to restrict modification of the first treatment cell to using only the treatment plan data;
modifying the first treatment cell control data using only the treatment plan data;
after the modification of the first treatment cell control data, unlocking the first treatment cell control data;
receiving a selection of a second treatment cell, wherein the selection of the second treatment cell is based on the planning data;
locking the second treatment cell control data of the second treatment cell in the database to limit modification of the second treatment cell control data using only the planning data;

modifying, using only the planning data, the second treatment cell control data using the planning data; and unlocking the second treatment cell control data in the database.

14. The non-transitory computer readable medium of claim 13, wherein the treatment system is a high intensity focused ultrasound system and the execution of the machine executable instructions further causes the processor to: control the high intensity focused ultrasound system to sonicate a target zone of a subject using the treatment system control data; modify the first treatment cell control data in response to only the treatment planning data and modify the second treatment cell control data in response to only the planning data during sonication of the target zone; and superimpose an ultrasound path indicative of a path of ultrasound from the high intensity focused ultrasound system to the target zone on the physician graphical user interface.

15. The non-transitory computer readable medium of claim 13, wherein the medical instrument further comprises a magnetic resonance imaging system for acquiring magnetic resonance imaging data from an imaging zone, wherein the execution of the machine executable instructions further cause the processor to control the magnetic resonance imaging system to acquire the medical image, wherein the execution of the machine executable instructions further causes the processor to repeatedly:

acquire thermal magnetic resonance data during sonication of the target zone;

reconstruct a thermal magnetic resonance image using the thermal magnetic resonance data; and superimpose the thermal magnetic resonance image on the medical image on the physician graphic user interface and the technician graphical user interface.

16. The non-transitory computer readable medium of claim 13, wherein the medical instrument further comprises a medical imaging system for acquiring the medical image, and wherein the execution of the machine executable instructions further causes the processor to control the medical imaging system to acquire the medical image.

17. A method of operating a medical instrument, wherein the medical instrument comprises a first display device, wherein the medical instrument further comprises a second display device, wherein the medical instrument further comprise a database, wherein the method comprises:

receiving a medical image;

displaying the medical image in a physician graphical user interface using the first display device;

displaying the medical image on a technician graphical user interface using the second display device;

wherein the method further comprises repeatedly:

receiving planning data from the physician graphical user interface, wherein the planning data is descriptive of a location in the medical image;

displaying the planning data on the technician graphical user interface;

receiving treatment plan data from the technician graphical user interface;

storing the treatment plan data in the database; and generating, using the treatment plan data in the database, treatment system control data for controlling a treatment system; and modifying the treatment system control data by operations including:

dividing at least a portion of the medical image into treatment cells, dividing the treatment system control data with reference to each of the treatment cells, wherein the treatment cells comprises a first treatment cell and a second treatment cell, wherein the divided treatment system control data comprises first treatment cell control data of the first treatment cell and second treatment cell control data of the second treatment cell, and wherein the database stores the first treatment cell control data and the second treatment cell control data;

receiving a selection of the first treatment cell using the treatment plan data;

locking the first treatment cell control data of the first treatment cell in the database to restrict modification of the first treatment cell control data to using only the treatment plan data;

modifying the first treatment cell control data using only the treatment plan data;

unlocking the first treatment cell control data, after the modification of the first treatment cell control data; receiving a selection of the second treatment cell using the planning data;

locking the second treatment cell control data in the database to limit modification of the second treatment cell control data using the only planning data;

modifying, using only the planning data, the second treatment cell control data; and after modification, unlocking the second treatment cell control data in the database.

18. The method of claim 17, wherein the treatment system is a high intensity focused ultrasound system and the method further includes: controlling the high intensity focused ultrasound system to sonicate a target zone of a subject using the control data; modifying the first treatment cell control data in response to only the treatment planning data and modifying the second treatment cell control data in response to only the planning data during sonication of the target zone; and superimposing an ultrasound path indicative of a path of ultrasound from the high intensity focused ultrasound system to the target zone on the physician graphical user interface.

19. The method of claim 17, wherein the medical instrument further comprises a magnetic resonance imaging system for acquiring magnetic resonance imaging data from an imaging zone, wherein the method further includes controlling the magnetic resonance imaging system to acquire the medical image, wherein the method further includes repeatedly:

acquiring thermal magnetic resonance data during sonication of the target zone;

reconstructing a thermal magnetic resonance image using the thermal magnetic resonance data; and superimposing the thermal magnetic resonance image on the medical image on the physician graphic user interface and the technician graphical user interface.

20. The method of claim 17, wherein the medical instrument further comprises a medical imaging system for acquiring the medical image, and wherein the method further includes controlling the medical imaging system to acquire the medical image.

* * * * *